United States Patent [19]

Székely et al.

[11] 4,451,483
[45] May 29, 1984

[54] 2,3,4-TRINOR-M-INTER-PHENYLENE-PROSTAGLANDIN DERIVATIVES AND COMPOSITIONS AND METHOD FOR INHIBITING BLOOD PLATELET AGGREGATION

[75] Inventors: István Székely, Dunakeszi; Krisztina Kékesi, Debrecen; Mariann Lovász neé Gáspár, Budapest; Sandor Botár, Budapest; Pál Hadházy, Budapest; István Rákóczi, Budapest; László Muszbek, Bebrecen; Judit Skopál, Budapest; István Stadler, Budapest; Károly Horváth, Budapest; Gábor Kovács, Budapest; Peter Körmöczy, Budapest, all of Hungary

[73] Assignee: Chinoin Gyogyszer es Vegyeszeti Termekek Gyara Rt., Budapest, Hungary

[21] Appl. No.: 367,068

[22] Filed: Apr. 9, 1982

[30] Foreign Application Priority Data

Apr. 14, 1981 [HU] Hungary ................. 962/81
Apr. 14, 1981 [HU] Hungary ................. 963/81
Apr. 14, 1981 [HU] Hungary ................. 964/81

[51] Int. Cl.³ .................. A61K 31/34; C07D 307/935
[52] U.S. Cl. .................. 424/285; 549/414; 549/465
[58] Field of Search ............. 424/285; 542/426, 429

[56] References Cited

U.S. PATENT DOCUMENTS 4,372,971  2/1983  Seipp et al. ............... 424/285

OTHER PUBLICATIONS

Hackh's Chem. Dictionary, 4th Ed., pp. 319 and 324.
Hawley, Condensed Chem. Dictionary, 10th Ed. (1981)–Van Nostrand Reinhold Co., p. 531.
*Prostacyclin*, John R. Vane, D.Sc and Sune Bergstrom, M.D., Raven Press, New York, pp. 17–29 (1979).

Primary Examiner—Henry R. Jiles
Assistant Examiner—Bernard Dentz
Attorney, Agent, or Firm—Karl F. Ross; Herbert Dubno

[57] ABSTRACT 2,3,4-trinor-1,5-inter-m-phenylene-prostacycline derivatives of the formula (I), wherein
$R^1$ is hydrogen, a $C_{1-4}$ alkyl group, an alkali metal cation or a primary, secondary, tertiary or quaternary ammonium cation,
$R^2$ and $R^3$ each represent hydrogen or a $C_{1-4}$ alkanoyl, benzoyl, substituted benzoyl, tetrahydropyranyl, ethoxyethyl or tri-($C_{1-4}$ alkyl)-silyl group,
$R^4$ is hydrogen or a $C_{1-4}$ alkyl group, and
$R^5$ is a hexyl, heptyl, phenoxymethyl or m-trifluoromethylphenoxymethyl group, or
$R^5$ represents a group of the general formula $$-\underset{\underset{Z}{|}}{C}H-R^6$$

and in this latter formula
Z is an amino group or an optionally halo-substituted $C_{1-4}$ alkanoylamino, benzoylamino or tosylamino group, and
$R^6$ is a $C_{4-6}$ alkyl, phenyl or benzyl group,
are prepared by reacting a bicyclic lactol of the formula (II), with a reactive phosphorane prepared from a triphenyl-m-carbobenzylphosphonium halide and a strong base, optionally esterifying the resulting prostaglandin derivative and, whenever it contains a free amino group, protecting this amino group by acylation, reacting then the prostaglandin derivative with an electrophilic reagent of the formula E-X, wherein X is halogen atom and E is halogen atom or an acetyl, trifluoroacetyl or N-succinimido group, and subjecting the resulting halogenated $PGI_1$ derivative to hydrogen halide elimination.

The compounds of the formula (I) possess valuable biological effects and can be applied in therapy primarily as blood platelet aggregation inhibiting agents.

24 Claims, No Drawings

2,3,4-TRINOR-M-INTER-PHENYLENE-PROSTAGLANDIN DERIVATIVES AND COMPOSITIONS AND METHOD FOR INHIBITING BLOOD PLATELET AGGREGATION

The invention relates to new 2,3,4-trinor-1,5-inter-m-phenylene-prostaglandin compounds and pharmaceutical compositions containing the same, as well as to a process for the preparation thereof.

The new compounds according to the invention correspond to the formula (I),

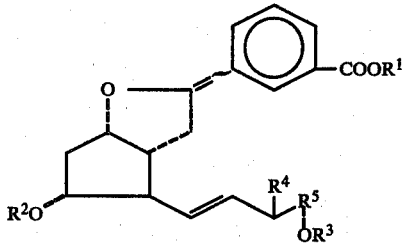

wherein
$R^1$ is hydrogen, a $C_{1-4}$ alkyl group, an alkali metal cation or a primary, secondary, tertiary or quaternary ammonium cation,
$R^2$ and $R^3$ each represent hydrogen or a $C_{1-4}$ alkanoyl, benzoyl, substituted benzoyl, tetrahydropyranyl, ethoxyethyl or tri-($C_{1-4}$ alkyl)-silyl group,
$R^4$ is hydrogen or a $C_{1-4}$ alkyl group, and
$R^5$ is a hexyl, heptyl, phenoxymethyl or m-trifluoromethylphenoxymethyl group, or
$R^5$ represents a group of the formula

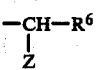

and in this latter formula
Z is an amino group or an optionally halo-substituted $C_{1-4}$ alkanoylamino, benzoylamino or tosylamino group, and
$R^6$ is a $C_{4-6}$ alkyl, phenyl or benzyl group.

The compounds of the formula (I) are prostacycline analogs and possess blood platelet aggregation inhibiting, thrombus, deaggregating, vasodilating, cytoprotective and ulcer healing effects.

Prostacycline (PGI$_2$) is an endogeneous substance. J. Vane et al. were the first to report its discovery [Nature 1976, 263, 663; Prostaglandins 1976 (12), 685, 897]. These authors also recognized that PGI$_2$ has anti-aggregating and deaggregating agonist functions in haemostatic regulation of the circulatory system.

Although the chemical synthesis of prostacycline has been elaborated by several research groups [see e.g. Angewandte Chemie International Edition 1978 (17), 293 and references cited therein], the introduction of prostacycline into therapy, such as for the prophylaxis of cardiac infarctions, is strongly restricted by the instability of the exocyclic enol ether present in the prostacycline structure. The sodium salt of prostacycline is a very stable, highly storable compound; the free PGI$_2$ acid, however, which is liberated from the sodium salt under physiological conditions, rapidly hydrolyzes into 6-keto-PGF$_{1\alpha}$, which does not possess the biological effects of PGI$_2$. The research work on prostacycline analogs is directed all over the world to the synthesis of molecules which are chemically more stable than PGI$_2$, and possibly exert more specific biological effects.

The 2,3,4-trinor-m-inter-phenylene-PGI$_2$ compounds of the present invention are much more stable chemically than prostacycline (with half-lines of some days even at pH=1). This can be attributed to the effect of the phenyl group in conjugated position to the enol ether, since the $\pi$ electronic system of the phenyl group suppresses the reactivity of the enol ether due to conjugation. Moreover, the rigid structure hinders the hydrolysis which is catalyzed by the carboxy group of prostacycline itself.

The new compounds of the formula (I) are prepared according to the invention in that a bicyclic lactol of the formula (II),

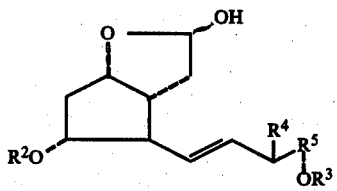

wherein $R^2$, $R^3$, $R^4$ and $R^5$ are as defined above, is reacted, in a dipolar aprotic solvent, with a phosphorane formed from a phosphonium salt of the formula (III),

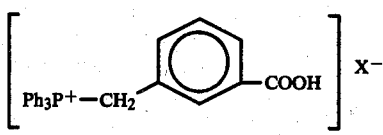

wherein Ph is phenyl and $X^-$ is a monovalent anion, with a strong base, the resulting prostaglandin derivative of the formula (IV),

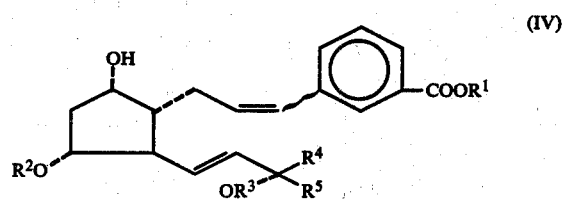

wherein $R^1$ is hydrogen and $R^2$, $R^3$, $R^4$ and $R^5$ are as defined above, is optionally esterified to obtain a derivative wherein $R^1$ is $C_{1-4}$ alkyl, and when the $R^5$ substituent of the resulting prostaglandin derivative contains a free amino group as Z, the compound is acylated with an acylating agent containing a trifluoroacetyl group, and a resulting prostaglandin derivative of the formula (IV), wherein $R^1$, $R^2$, $R^3$, $R^4$ and $R^5$ are as defined in connection with the formula (I) with the proviso that when $R^5$ is a group of the formula

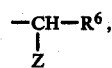

Z may not represent a free amino group, is treated with an electrophilic reagent of the formula E-X, wherein X is a halogen atom and E is a halogen atom or an acetyl, trifluoroacetyl or N-succinimido group, in an organic solvent or in a two-phase medium containing water and a water-immiscible organic solvent, if necessary, in the presence of an acid binding agent, and the resulting halogenated $PGI_1$ derivative of the formula (V),

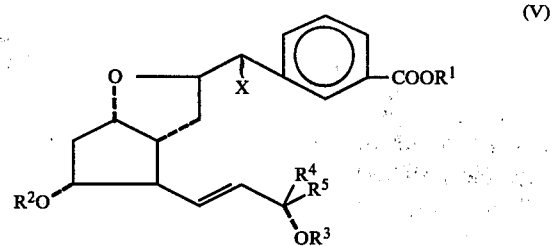

wherein X is halogen atom and $R^1$, $R^2$, $R^3$ and $R^4$ are as defined in connection with the formula (I) with the proviso that if $R^5$ stands for a group of the formula

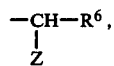

Z may not represent a free amino group, is reacted with a basic substance, and, if desired, a resulting compound of the formula (I) is converted into another compound of the formula (I) by saponification, salt-formation, acylation or deacylation.

The starting substances of the formula (II) are the appropriately substituted derivatives of 3,3α,β,4,5,6-,6αβ-hexahydro-2-hydroxy-4β-(3-hydroxy-1-transoctenyl)-5α-hydroxy-2H-cyclopenta[b]furan, a known intermediate of the synthesis of prostaglandin compounds. These intermediates can be prepared by methods well known in the art [see e.g. Prostaglandin Research, 237–239 (ed. P. Crabbe, Academic Press, 1977); J. S. Bindra, R. Bindra: Prostaglandin Synthesis, Academic Press 1977, p. 462 and Chapter 10].

The compounds of the formula (II) are reacted, in a dipolar non-protic solvent, with a reactive phosphorane compound prepared in situ from a triphenyl-m-carbobenzylphosphonium halide and a strong base to form 2,3,4-trinor-m-inter-phenylene-$PGF_{2\alpha}$ derivatives of the formula (IV).

Whenever the resulting compound of the formula (IV) contains a free amino group in substituent $R^5$, this free amino group is first protected by acylation, and then the compound is reacted with an electrophilic reagent of the formula E-X to obtain a cyclic 2,3,4-trinor-m-inter-phenylene-$PGI_1$ derivative of the formula (V). As electrophylic reagent of the formula E-X e.g. iodine, bromine, N-bromosuccinimide or N-chlorosuccinimide can be applied; thus X may stand for chlorine, bromine or iodine atom in the resulting cyclic derivative of the formula (V).

Thereafter, the $PGI_1$ derivative of the formula (V) is subjected to hydrogen halide elimination to obtain the desired 2,3,4-trinor-m-inter-phenylene-$PGI_2$ derivative of the formula (I). Elimination is performed by contacting the cyclic halo compound with a base, such as an alkali metal carbonate (e.g. potassium carbonate), an alkali metal hydrocarbonate (e.g. sodium hydrocarbonate), an alkali metal hydroxide (e.g. potassium hydroxide), a tertiary amine (e.g. triethyl amine or pyridine), furthermore 1,5-diazabicyclo[4.3.0]-non-5-ene (DBN) or 1,5-diazabicyclo[5.4.0]undec-5-ene (DBU).

The resulting products can be purified easily by column chromatography on silica gel.

If a compound of the formula (I) in which $R^2$ and/or $R^3$ is other than hydrogen is to be prepared, one can proceed so that the respective 2,3,4-trinor-m-inter-phenylene-$PGI_1$ compound of the formula (V), which contains free hydroxy groups in positions 11 and 15, is converted into the appropriate protected derivative first, and then it is subjected to hydrogen halide elimination. As an alternative solution, a compound of the formula (I) with free hydroxy groups in positions 11 and 15 is prepared first, and then it is subjected to acylation, tetrahydropyranylation, ethoxyethylation or silylation.

The compounds in which $R^1$ is a straight-chain or branched $C_{1-4}$ alkyl group can be prepared from the respective carboxylic acids by methods known per se, e.g. applying diazoalkane reactants.

The compounds in which $R^1$ is an alkali metal cation or a primary, secondary, tertiary or quaternary ammonium ion can be prepared by reacting the free acids with the appropriate bases or amines.

The compounds in which $R^1$ is an alkali metal cation can also be prepared by subjecting the esters to hydrolysis.

The compounds of the formula (I) in which $R^5$ is a group of the formula

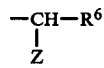

and Z stands for a free amino group can be prepared most easily by deprotecting the respective protected amino derivative in the last step of the synthesis. Of the amino protecting groups the $C_{1-4}$ alkanoyl, $C_{1-4}$ haloalkanoyl, alkoxycarbonyl, benzoyl, tosyl, benzyloxycarbonyl, and p-nitrophenoxycarbonyl groups are preferred, these being able to be split off easily by methods known per se.

If a compound of the formula (II) in which $R^5$ is a group of the general formula

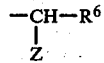

and Z stands for trifluoroacetylamino group is applied as starting substance, the trifluoroacetyl protecting group also splits off under the conditions of hydrogen halide elimination, yielding the respective compound of the formula (I) with a free amino group in position 16.

The term "a $C_{1-4}$ alkyl group" as used in the specification refers to methyl, ethyl, n-propyl, isopropyl, n-butyl, isobutyl, sec.-butyl and tert.-butyl groups. The optionally halogen-substituted $C_{1-4}$ alkanoyl groups are groups derived from alkanes corresponding to the above $C_{1-4}$ alkyl groups, which may contain one or more halogen substituents. The term "halogen atom" refers to fluorine, chlorine, bromine and iodine atoms. The substituted benzoyl group may have halo or phenyl substituents. The alkyl groups present in the tri-($C_{1-4}$ alkyl)silyl moieties may be the same or different. The term "a $C_{4-6}$ alkyl group" refers to n-butyl, n-pentyl and n-hexyl groups and branched isomers thereof.

When $R^1$ is an alkali metal cation, this cation may be a sodium, lithium or potassium ion. The term "a primary, secondary, tertiary or quaternary ammonium ion" refers to ions derived from non-cyclic or cyclic organic amines containing one or more nitrogen atoms, wherein, depending on the order of the amine, the nitrogen atom bears one, two, three or four $C_{1-4}$ alkyl or $C_{5-8}$ cycloalkyl (such as cyclopentyl, cyclohexyl, cycloheptyl or cyclooctyl) substituents. The alkyl substituents attached to the nitrogen atom may also bear substituents, preferably hydroxy groups.

The main pharmacological effect of the new compounds according to the invention is that, like $PGI_2$, they inhibit blood platelet aggregation and are able to dissolve the already existing agglomerates. The aggregation inhibiting effects of the new compounds were examined on human and guinea pig platelet rich plasma (PRP) according to the method of Born. Aggregation was provoked by adding 4 μmol/ml of ADP to the plasma, and then the prostacycline concentrations required to attain 50% or 100% inhibiting effect ($IC_{50}$ or $IC_{100}$) were determined. The results of the tests, wherein $PGI_2$ sodium salt was used as reference substance, are given in Table 1.

TABLE 1

| Active agent | $IC_{50}$ on human PRP | $IC_{100}$ on guinea pig PRP |
|---|---|---|
| $PGI_2$ sodium salt | 2 ng/ml | 1.75 ng/ml |
| 5(Z)—2,3,4-trinor-1,5-inter-m-phenylene-20-methyl-$PGI_2$ sodium salt | 12.5 ng/ml | 14 ng/ml |

Although the new compounds according to the invention are less potent in aggregation-inhibiting effect than $PGI_2$ sodium salt, they are particularly valuable in therapy, since in aqueous media they are significantly more stable than $PGI_2$. The biological half-life (i.e. the period within which the biological activity of the substance drops to the half) is 3 minutes for $PGI_2$ an an aqueous medium at pH=7, and about 7 days for the new compounds according to the invention.

The new compounds according to the invention can be converted into pharmaceutical compositions by methods known per se, utilizing conventional pharmaceutical diluents, carriers, filling agents, formulation aids and other additives. These compositions may contain, depending on the manner and frequency of administration, fractions or multiples of the effective dose of the active agent.

The invention is elucidated in detail by the aid of the following non-limiting Examples.

EXAMPLE 1

Preparation of 2,3,4,17,18,19,20-heptanor-1,5-inter-m-phenylene-11,15-bis(tetrahydropyranyloxy)-16-phenoxy-$PGF_{2\alpha}$ methyl ester 250 mg (10.41 mmoles) of sodium hydride are introduced into a dried three-necked flask equipped with a thermometer, a magnetic stirrer and a rubber cap. The flask is flushed with nitrogen gas, and then 5 ml of dry dimethyl sulfide are added. The flask is connected to a nitrogen cylinder, and nitrogen is introduced into the flask in a slow stream, through a mercury-sealed bubbler, to attain a slight nitrogen overpressure. Thereafter the suspension is warmed slowly to 60° C., whereupon gas evolution occurs. When the gas evolution ceases (after about 0.5 hours) the mixture is warmed to 70° C. and stirred at this temperature for 0.5 hours. The resulting dark grey solution is cooled to 15° C., and 2.45 g (5.68 mmoles) of m-carboxybenzyl-triphenyl-phosphonium chloride, pre-dried in vacuo, are added. The resulting red solution is stirred at room temperature for 0.5 hours, and then a solution of 1.57 g (2.59 mmoles) of 3,3aβ,4,5,6,6aβ-hexahydro-2-hydroxy-4β-(3-tetrahydropyranyloxy-4-phenoxy-butenyl)-5α-tetrahydropyranyloxy-2H-cyclopenta[b]furan in 500 μl of dry dimethyl sulfoxide is added. The reaction mixture is stirred at 60° C. for one hour, and poured then onto a mixture of 20 g of ice and 50 ml of water. The resulting solution is extracted twice with 10 ml of ether, each, then the pH of the aqueous phase is adjusted to 4–5 with 2 n aqueous sodium bisulfate solution, and the aqueous phase is extracted four times with 20 ml of ether, each, and twice with 20 ml of ethyl acetate, each. The organic phases are combined, dried over sodium sulfate, filtered, and the filtrate is evaporated under reduced pressure. The resulting 2.5 g of crude product are dissolved in 20 ml of ether, the solution is cooled to 0° C., and an etheral diazomethane solution is added dropwise, under stirring, until the yellow color of diazomethane remains persistent. The progress of the reaction is monitored by thin layer chromatography using silica gel G as adsorbent and a 20:10:1 mixture of benzene, dioxane and acetic acid as eluting agent (the $R_f$ value of the free acid is 0.52 and that of the methyl ester is 0.73), and if the reaction is still incomplete, more etheral diazomethane solution are added to the mixture.

Ether is distilled off, and the resulting crude methyl ester is subjected to chromatography on a column filled with silica gel. A 2:1 mixture of benzene and ethyl acetate is applied as eluting agent. Fractions of the effluent are examined by thin layer chromatography, using silica gel G as adsorbent and a 20:10:1 mixture of benzene, dioxane and acetic acid as eluting agent. The fractions which contain a substance with an $R_f$ value of 0.73 are combined and evaporated. 1.426 g (70%) of the named compound are obtained: $R_f$=0.73 (on silica gel G plate, using a 20:10:1 mixture of benzene, dioxane and acetic acid as eluting agent).

EXAMPLE 2

Preparation of 2,3,4,17,18,19,20-heptanor-1,5-inter-m-phenylene-16-phenoxy-$PGF_{2\alpha}$ methyl ester One proceeds as described in Example 1 with the difference that a solution of 350 mg (1.29 mmoles) of 3,3aβ,4,5,6,6aβ-hexahydro-2-hydroxy-4β-(3-hydroxy-4-phenoxy-1-trans-1-butenyl)-5α-hydroxy-2H-cyclopenta[b]furan in 450 μl of dry dimethyl sulfoxide is added to the reaction mixture. 401.9 mg (77.5%) of the named compound are obtained.

NMR (CDCl$_3$): δ=6.85–7.5 (m, 7H, aromatic protons), 7.5–8.05 (m, 2H, aromatic protons), 5.25–6.75 (m, 4H, olefin protons), 3.92 (s, 3H, OC$\underline{H}_3$) ppm.

Similarly can be prepared the following compounds: 2,3,4,17,18,19,20-Heptanor-1,5-inter-m-phenylene-16-(m-trifluoromethyl-phenoxy)-$PGF_{2\alpha}$ methyl ester.

NMR (CDCl$_3$): δ=7,1–7,5 (m, 5H, aromatic protons), 7.5–8.05 (m, 3H, aromatic protons) ppm. 2,3,4-Trinor-1,5-inter-m-phenylene-20-methyl-$PGF_{2\alpha}$ methyl ester.

NMR (CDCl$_3$): δ=0.89 (t, 3H, C$\underline{H}_3$), 3.90 (s, 3H, OC$\underline{H}_3$), 5.23–6.7 (m, 4H, olefin protons), 7.2–7.55 (m, 2H, aromatic protons), 7.6–8.05 (m, 2H, aromatic protons) ppm.

$R_f$=0.34 (benzene:dioxane:acetic acid 20:10:1)

2,3,4-Trinor-1,5-inter-m-phenylene-20-ethyl-PGF$_{2\alpha}$ methyl ester.

R$_f$=0.35 (benzene:dioxane:acetic acid 20:10:1)

EXAMPLE 3

Preparation of
2,3,4,18,19,20-hexanor-1,5-inter-m-phenylene-11,15-bis(tetrahydropyranyloxy)-16-acetylamino-17-phenyl-PGF$_{2\alpha}$ methyl ester One proceeds as described in Example 1 with the difference that a solution of 1.37 g (2.59 mmoles) of 3,3α$\beta$,4,5,6,6α$\beta$-hexahydro-2-hydroxy-4$\beta$-(3-tetrahydropyranyloxy-4-acetamido-5-phenyl-1-trans-pentanyl)-5α-tetrahydropyranyloxy-2H-cyclopenta[b]furan in 400 μl of dry dimethyl sulfoxide is added to the reaction mixture. 1.426 g (70%) of the title compound are obtained. R$_f$=0.05 (adsorbent: silica gel G (Merk), solvent:benzene:dioxane:acetic acid 20:10:1).

EXAMPLE 4

Preparation of
2,3,4-trinor-1,5-inter-m-phenylene-16-amino-PGF$_{2\alpha}$ methyl ester (a) One proceeds as described in Example 2 with the difference that a solution of 0.497 g (1.29 mmoles) of 3,3α$\beta$,4,5,6,6α$\beta$-hexahydro-2-hydroxy-4$\beta$-[3-hydroxy-4-(tert.-butoxycarbonylamino)-1-trans-octenyl]-5α-hydroxy-2H-cyclopenta[b]furan in 400 μl of dry dimethyl sulfoxide is added to the reaction mixture. 0.450 g (87%) of 2,3,4-trinor-1,5-inter-m-phenylene-16-(tert.-butoxycarbonylamino)-PGF$_{2\alpha}$ methyl ester are obtained; R$_f$=0.31 (adsorbent: silica gel G, solvent: ethyl acetate:benzene 4:1).

Similarly can be prepared the following compounds:
2,3,4,17,18,19,20-Heptanor-1,5-inter-m-phenylene-16-phenyl-16-(tert.-butoxycarbonylamino)-PGF$_{2\alpha}$ methyl ester, R$_f$=0.35 (ethyl acetate:benzene 4:1); and 2,3,4,18,19,20-hexanor-1,5-inter-m-phenylene-16-(tert.-butoxycarbonylamino)-17-phenyl-PGF$_{2\alpha}$ methyl ester, R$_f$=0.36 (ethyl acetate:benzene 4:1).

(b) 0.450 g (0.87 mmoles) of 2,3,4-trinor-1,5-inter-m-phenylene-16-(tert.-butoxycarbonylamino)-PGF$_{2\alpha}$ methyl ester are dissolved in 5 ml of acetic acid, and 1.05 equivalents of dry hydrochloric acid gas are introduced into the solution. The end-point of the reaction is when no more isobutylene gas evolves from the mixture. Thereafter the mixture is diluted with 50 ml of ethyl acetate, and the pH of the mixture is adjusted to 8-9 with 1 n sodium hydroxide solution under intense stirring. The aqueous phase is removed, the organic phase is dried over anhydrous sodium sulfate and then evaporated. The resulting crude product is subjected to chromatography on silica gel column, using a 8:1 mixture of isopropanol and water as eluting agent. The effluent fractions are subjected to thin layer chromatography using a 7:2 mixture of isopropanol and water as solvent. The fractions which contain a substance with an R$_f$ value of 0.4 are combined and evaporated. 0.291 g of the named compound are obtained.

Similarly can be prepared the following compounds:
2,3,4,17,18,19,20-Heptanor-1,5-inter-m-phenylene-16-amino-16-phenyl-PGF$_{2\alpha}$ methyl ester, R$_f$=0.45 (isopropanol:water 7:2), and
2,3,4,18,19,20-hexanor-1,5-inter-m-phenylene-16-amino-17-phenyl-PGF$_{2\alpha}$ methyl ester, R$_f$=0.47 (isopropanol:water 7:2).

EXAMPLE 5

Preparation of
2,3,4-trinor-1,5-inter-m-phenylene-16-acetylamino-PGF$_{2\alpha}$ methyl ester 2.5 g (5.92 mmoles) of 16-amino-2,3,4-trinor-1,5-inter-m-phenylene-PGF$_{2\alpha}$ methyl ester are dissolved in 3 ml of dry pyridine. The solution is cooled to 0° C., 0.98 g (0.79 ml, 12.5 mmoles) of acetyl chloride are added to it dropwise, and then the mixture is stirred at 0° C. for 30 minutes. The mixture is diluted with 50 ml of ethyl acetate. The organic phase is washed with 10 ml of 1 n hydrochloric acid solution, dried over anhydrous magnesium sulfate, filtered, and the filtrate is evaporated under reduced pressure. 2.36 g (86%) of the named compound are obtained; R$_f$=0.7 (isopropanol:water 7:2).

Similarly can be prepared the following compounds:
2,3,4-trinor-1,5-inter-m-phenylene-16-benzoylamino-PGF$_{2\alpha}$ methyl ester, R$_f$=0.67 (isopropanol:water 7:2), and
2,3,4-trinor-1,5-inter-m-phenylene-16-tosylamino-PGF$_{2\alpha}$ methyl ester, R$_f$=0.61 (isopropanol:water 7:2).

EXAMPLE 6

Preparation of
2,3,4,17,18,19,20-heptanor-1,5-inter-m-phenylene-5-iodo-16-phenoxy-PGI$_1$ methyl ester 355 mg (0.81 mmoles) of 2,3,4,17,18,19,20-heptanor-1,5-inter-m-phenylene-16-phenoxy-PGF$_{2\alpha}$ methyl ester are dissolved in 5 ml of dry dichloromethane. 4.05 ml (4.05 mmoles) of a 1 m aqueous sodium hydrocarbonate solution are added to the mixture, and the resulting two-phase mixture is stirred vigorously at 0° C. 16.4 ml of a 0.0976 molar iodine solution in dichloromethane (=1.62 mmoles of iodine) are added to the stirred mixture at 0° C. within 15 minutes, and then the mixture is stirred at room temperature for 3 hours. 5% aqueous sodium thiosulfate solution is added then to the mixture until the color of iodine disappears, and the aqueous phase is extracted then thrice with 50 ml of ether, each, and 20 ml of ethyl acetate. The organic phases are combined, dried over sodium sulfate, filtered, and the solvent is evaporated under reduced pressure. 530 mg of the crude product are obtained.

The crude product is subjected to column chromatography on silica gel (100 g of Merck Art. No. 7731 grade silica gel with a particle size of 0.03-0.2 mm), applying ethyl acetate as eluting agent. The effluent is analyzed by thin layer chromatography on Merck Art. No. 5715 plates, the fractions which contain a substance with an R$_f$ value of 0.49 and 0.47 are combined, and the solvent is evaporated under reduced pressure. 493 mg (87%) of the named compound are obtained as two fractions (endo and exo isomers); R$_f$=0.49 and 0.47 (adsorbent: Merck Art. No. 5715 type silica gel G plate, solvent: ethyl acetate).

Similarly can be prepared the following compounds:
2,3,4,17,18,19,20-heptanor-1,5-inter-m-phenylene-5-iodo-16-(3-trifluoromethylphenoxy)-PGI$_1$ methyl ester, R$_f$=0.51 and 0.48 (ethyl acetate);
2,3,4-trinor-1,5-inter-m-phenylene-5-iodo-16-acetylamino-PGI$_1$ methyl ester, R$_f$=0.6 (isopropanol:water 7:2);

2,3,4-trinor-1,5-inter-m-phenylene-5-iodo-16-benzoylamino-PGI$_1$ methyl ester, R$_f$=0.63 (isopropanol:water 7:2);

2,3,4-trinor-1,5-inter-m-phenylene-5-iodo-16-tosylamino-PGI$_1$ methyl ester, R$_f$=0.56 (isopropanol:water 7:2);

2,3,4-trinor-1,5-inter-m-phenylene-5-iodo-20-methyl-PGI$_1$ methyl ester, R$_f$=0.43 and 0.40 (ethyl acetate);

2,3,4-trinor-1,5-inter-m-phenylene-5-iodo-20-ethyl-PGI$_1$ methyl ester, R$_f$=0.43 and 0.41 (ethyl acetate);

2,3,4,17,18,19,20-heptanor-1,5-inter-m-phenylene-5-iodo-11,15-diacetoxy-16-phenoxy-PGI$_1$ methyl ester, R$_f$=0.7 and 0.74 (benzene:ethyl acetate 1:1).

EXAMPLE 7

Preparation of 2,3,4-trinor-1,5-inter-m-phenylene-5-bromo-16-amino-PGI$_1$ methyl ester 460 mg (1.1 mmoles) of 2,3,4-trinor-1,5-inter-m-phenylene-16-amino-PGF$_{2\alpha}$ methyl ester are dissolved in 3 ml of dry triethyl amine, the solution is cooled to 0° C., and 160 μl (1.15 mmoles) of dry trifluoroacetic acid are added. The reaction mixture is stirred at 0° C. for 30 minutes and then diluted with 50 ml of ethyl acetate. The organic phase is washed twice with 10 ml of 1 n aqueous oxalic acid solution, each, dried over anhydrous magnesium sulfate, filtered, and the filtrate is evaporated under reduced pressure. The resulting crude 2,3,4-trinor-1,5-inter-m-phenylene-16-trifluoroacetamido-PGF$_{2\alpha}$ methyl ester is dissolved in 5 l ml of a 1:1 mixture of dry chloroform and tetrahydrofuran. The solution is cooled to −78° C. in an acetone/solid carbon dioxide bath, and 215.4 mg (1.21 mmoles) of solid N-bromo-succinimide are added in a single portion to the mixture under stirring in inert gas atmosphere. The mixture is stirred at −78° C. for 10 minutes, thereafter the cooling bath is removed and the mixture is allowed to warm to room temperature. The mixture is stirred at room temperature for 30 minutes, diluted with 50 ml of chloroform, and washed thrice with 20 ml of water, each. The organic phase is dried over anhydrous sodium sulfate, filtered, and the filtrate is evaporated under reduced pressure. 680 mg of 2,3,4-trinor-1,5-inter-m-phenylene-5-bromo-16-trifluoroacetamido-PGI$_1$ methyl ester are obtained; R$_f$=0.35 (ethyl acetate:benzene 3:1).

This crude product is added to 2 ml of a 0.03 molar potassium hydrocarbonate solution (solvent: a 95:5 mixture of water and methanol), the mixture is stirred for 60 minutes, and extracted then five times with 5 ml of ethyl acetate, each. The organic phases are combined, dried over potassium carbonate, filtered, and the filtrate is evaporated under reduced pressure. 395 mg (72%) of the named compound are obtained; R$_f$=0.45 (isopropanol:water 7:2).

Similarly can be prepared the following compounds:
2,3,4,17,18,19,20-heptanor-1,5-inter-m-phenylene-5-bromo-16-amino-16-phenyl-PGI$_1$ methyl ester, R$_f$=0.49 (isopropanol:water 7:2);

2,3,4,18,19,20-hexanor-1,5-inter-m-phenylene-5-bromo-16-amino-17-phenyl-PGI$_1$ methyl ester, R$_f$=0.47 (isopropanol:water 7:2).

EXAMPLE 8

Preparation of 2,3,4,17,18,19,20-heptanor-1,5-inter-m-phenylene-16-phenoxy-PGI$_2$ methyl ester A mixture of 230.4 mg (0.40 mmoles) of 2,3,4,17,18,19,20-heptanor-1,5-inter-m-phenylene-5-iodo-16-phenoxy-PGI$_1$ methyl ester and 2 ml of distilled 1,5-diazabicyclo[4.3.0]non-5-ene is stirred at 50° C. for one hour. The reaction mixture is diluted with 50 ml of ether and washed twice with 20 ml of water, each. The organic phase is dried over sodium sulfate, filtered, and the filtrate is evaporated under reduced pressure. A crude product, weighing 210 mg, is obtained.

The resulting crude product is subjected to column chromatography on 60 g of silica gel (Merck Art. No. 7734, particle size: 0.03–0.2 mm), applying a 3:1 mixture of ether and acetone as eluting agent. The effluent is analyzed by thin layer chromatography, applying silica gel G (Merck Art. No. 5715) as adsorbent and ethyl acetate as solvent. The fractions which contain a substance with an R$_f$ value of 0.49 and 0.51 are combined and evaporated under reduced pressure. 152.1 mg (85.4%) of the named compound are obtained. When subjected to thin layer chromatography on silica gel G (Merck Art. No. 5717) in ethyl acetate, the Z isomer appears at R$_f$=0.51 and the E isomer appears at R$_f$=0.49.

Similarly can be prepared the following compounds:
2,3,4,17,18,19,20-heptanor-1,5-inter-m-phenylene-16-(3-trifluoromethyl-phenoxy)-PGI$_2$ methyl ester, R$_f$=0.51 and 0.53 (ethyl acetate);

2,3,4-trinor-1,5-inter-m-phenylene-16-amino-PGI$_2$ methyl ester, R$_f$=0.45 (isopropanol:water 7:3);

2,3,4-trinor-1,5-inter-m-phenylene-16-acetamido-PGI$_2$ methyl ester, R$_f$=0.70 (isopropanol:water 7:3);

2,3,4-trinor-1,5-inter-m-phenylene-16-benzoylamino-PGI$_2$ methyl ester, R$_f$=0.74 (isopropanol:water 7:3);

2,3,4,17,18,19,20-heptanor-1,5-inter-m-phenylene-16-amino-16-phenyl-PGI$_2$ methyl ester, R$_f$=0.49 (isopropanol:water 7:3);

and 2,3,4,18,19,20-hexanor-1,5-inter-m-phenylene-16-amino-17-phenyl-PGI$_2$ methyl ester, R$_f$=0.53 (isopropanol:water 7:3).

EXAMPLE 9

Preparation of 5(Z)-2,3,4,17,18,19,20-heptanor-1,5-inter-m-phenylene-16-phenoxy-PGI$_2$ sodium salt 338.7 mg (0.78 mmoles) of 5(Z)-2,3,4,17,18,19,20-heptanor-1,5-inter-m-phenylene-PGI$_2$ methyl ester are dissolved in 2 ml of methanol, and 1.86 ml (0.93 mmoles) of a 0.5 molar methanolic sodium hydroxide solution are added to the mixture. The mixture is stirred for 6 hours at room temperature, and methanol is then distilled off under reduced pressure. The solid residue is suspended in petroleum ether, and petroleum ether is decanted. 340.4 mg (98%) of the named compound are obtained; R$_f$=0.43 (in a 20:10:1 mixture of benzene, dioxane and acetic acid).

NMR (CD$_3$OD): δ=5.32 (broad s, 1H, proton in position 5), 5.45-5.77 (m, 2H, olefin protons), 6.9-7.5 (m, 6H, aromatic protons), 7.5-8.15 (m, 3H, aromatic protons) ppm.

Similarly can be prepared the following compounds:
5(E)-2,3,4,17,18,19,20-Heptanor-1,5-inter-m-phenylene-16-phenoxy-PGI$_2$ sodium salt, R$_f$=0.41 (in a 20:10:1 mixture of benzene, dioxane and acetic acid). NMR (CD$_3$OD): δ=5.5-5.7 (m, 2H, olefin protons), 5.95 (broad s, 1H, proton in position 5), 6.9-8.15 (m, 9H, aromatic protons) ppm. 5(E,Z)-2,3,4,17,18,19,20-Heptanor-1,5-inter-m-phenylene-16-(3-trifluoromethyl-phenoxy)-PGI$_2$ sodium salt, R$_f$=0.47 (in a 20:10:1 mixture of benzene, dioxane and acetic acid). 5(Z)-2,3,4-Trinor-1,5-inter-m-phenylene-20-methyl-PGI$_2$ sodium salt, R$_f$=0.42 (in a 20:10:1 mixture of benzene, dioxane and acetic acid). NMR (CD$_3$OD): δ=0.89 (t, 3H, CH$_3$), 5.25 (s, 1H, proton in position 5) ppm. 5(E)-2,3,4-Trinor-1,5-inter-m-phenylene-20-methyl-PGI$_2$ sodium salt; R$_f$=0.40 (in a 20:10:1 mixture of benzene, dioxane and acetic acid). NMR (CD$_3$OD): δ=0.89 (t, 3H, CH$_3$), 5.90 (s, 1H, proton in position 5) ppm. 5(E,z)-2,3,4-Trinor-1,5-inter-m-phenylene-20-ethyl-PGI$_2$ sodium salt, R$_f$=0.44 and 0.41 (in a 20:10:1 mixture of benzene, dioxane and acetic acid). 2,3,4-Trinor-1,5-inter-m-phenylene-16-amino-PGI$_2$ sodium salt, R$_f$=0.3 (in a 7:3 mixture of isopropanol and water). 2,3,4-Trinor-1,5-inter-m-phenylene-16-acetamido-PGI$_2$ sodium salt, R$_f$=0.6 (in a 7:3 mixture of isopropanol and water). 2,3,4-Trinor-1,5-inter-m-phenylene-16-benzoylamino-PGI$_2$ sodium salt, R$_f$=0.61 (in a 7:3 mixture of isopropanol and water). 2,3,4-Trinor-1,5-inter-m-phenylene-16-tosylamino-PGI$_2$ sodium salt, R$_f$=0.55 (in a 7:3 mixture of isopropanol and water). 2,3,4,17,18,19,20-Heptanor-1,5-inter-m-phenylene-16-amino-16-phenyl-PGI$_2$ sodium salt, R$_f$=0.36 (in a 7:3 mixture of isopropanol and water). 2,3,4,18,19,20-Hexanor-1,5-inter-m-phenylene-16-amino-17-phenyl- PGI$_2$ sodium salt, R$_f$=0.38 (in a 7:3 mixture of isopropanol and water).

EXAMPLE 10

Preparation of 5(Z)-2,3,4,17,18,19,20-heptanor-1,5-inter-m-phenylene-16-phenoxy-PGI$_2$ dicyclohexylamine salt 399 mg (0.906 mmoles) of 5(Z)-2,3,4,17,18,19,20-heptanor-1,5-inter-m-phenylene-16-phenoxy-PGI$_2$ sodium salt are dissolved in 5 ml of water, and then 5 ml of a saturated aqueous sodium chloride solution and 20 ml of ethyl acetate are added. The mixture is cooled to 0° C. and 1 molar aqueous oxalic acid is added to the stirred mixture to adjust its pH to 4-5. The phases are separated from each other, the aqueous phase is extracted thrice with 20 ml of ethyl acetate, each, the organic phases are combined, dried over sodium sulfate, filtered, and the filtrate is evaporated under reduced pressure.

The resulting free acid is dissolved in 2.5 ml of ether, and a solution of 195 mg (1.08 mmoles) of dicyclohexylamine in 1 ml of ether is added at room temperature. The solvent is distilled off under reduced pressure, the residue is triturated with petroleum ether, and the liquid is decanted. 528 mg (97%) of the named compound are obtained; R$_f$=0.43 (in a 20:10:1 mixture of benzene, dioxane and acetic acid).

The following compounds can be similarly prepared:
5(Z)-2,3,4,17,18,19,20-heptanor-1,5-inter-m-phenylene-16-phenoxy-PGI$_2$ ammonium salt, R$_f$=0.59 (in a 20:10:1 mixture of benzene, dioxane and acetic acid);
5(Z)-2,3,4,17,18,19,20-heptanor-1,5-inter-m-phenylene-16-phenoxy-PGI$_2$ dimethylamine salt, R$_f$=0.43 (in a 20:10:1 mixture of benzene, dioxane and acetic acid);
5(Z)-2,3,4,17,18,19,20-heptanor-1,5-inter-m-phenylene-16-phenoxy-PGI$_2$ tetrabutylammonium salt, R$_f$=0.43 (in a 20:10:1 mixture of benzene, dioxane and acetic acid); and
5(Z)-2,3,4,17,18,19,20-heptanor-1,5-inter-m-phenylene-16-phenyoxy-PGI$_2$ tris(hydroxymethyl)-methylammonium salt, R$_f$=0.59 (in a 20:10:1 mixture of benzene, dioxane and acetic acid.)

What we claim is:

1. A 2,3,4-trinor-1,5-inter-m-phenylene-prostacycline derivative of the formula (I)

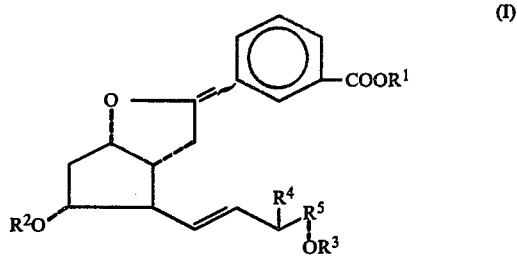

wherein
R$^1$ is hydrogen, C$_{1-4}$alkyl, an alkali metal cation or a primary, secondary, tertiary or quaternary ammonium cation, R$^2$ and R$^3$ each are hydrogen or C$_{1-4}$alkanoyl, benzoyl, tetrahydropyranyl, ethoxyethyl or tri-(C$_{1-4}$alkyl)-silyl,
R$^4$ is hydrogen or C$_{1-4}$ alkyl, and
R$^5$ is hexyl, heptyl, phenoxymethyl or m-trifluoromethyl-phenoxymethyl, or
R$^5$ represents a group of the formula

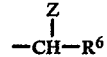

and
Z is amino, or unsubstituted or halo-substituted C$_{1-4}$ alkanoylamino, benzoylamino or tosylamino, and
R$^6$ is C$_{4-6}$alkyl, phenyl or benzyl.

2. 2,3,4,17,18,19,20-Heptanor-1,5-inter-m-phenylene-16-phenoxy-PGI$_2$ methyl ester as defined in claim 1.

3. 2,3,4,17,18,19,20-Heptanor-1,5-inter-m-phenylene-16-(3-trifluoromethyl-phenoxy)-PGI$_2$ methyl ester as defined in claim 1.

4. 2,3,4-Trinor-1,5-inter-m-phenylene-16-amino-PGI$_2$ methyl ester as defined in claim 1.

5. 2,3,4-Trinor-1,5-inter-m-phenylene-16-acetamido-PGI$_2$ methyl ester as defined in claim 1.

6. 2,3,4-Trinor-1,5-inter-m- phenylene-16-benzoylamino-PGI$_2$ methyl ester as defined in claim 1.

7. 2,3,4,17,18,19,20-Heptanor-1,5-inter-m-phenylene-16-amino-16phenyl PGI$_2$ methyl ester as defined in claim 1.

8. 2,3,4,18,19,20-Hexanor-1,5-inter-m-phenylene-16-amino-17-phenyl-PGI$_2$ methyl ester as defined in claim 1.

9. 5(Z)-2,3,4,17,18,19,20-Heptanor-1,5-inter-m-phenylene-16-phenoxy-PGI$_2$ sodium salt as defined in claim 1.

10. 5(E)-2,3,4,17,18,19,20-Heptanor-1,5-inter-m-phenylene-16-phenoxy-PGI$_2$ sodium salt as defined in claim 1.

11. 2,3,4,17,18,19,20-Heptanor-1,5-inter-m-phenylene-16-(3-trifluoromethyl-phenoxy)-PGI$_2$ sodium salt as defined in claim 1.

12. 2,3,4-Trinor-1,5-inter-m-phenylene-16-amino-PGI$_2$ sodium salt as defined in claim 1.

13. 2,3,4-Trinor-1,5-inter-m-phenylene-16-acetamido-PGI$_2$ sodium salt as defined in claim 1.

14. 2,3,4-Trinor-1,5-inter-m-phenylene-16-benzoylamino-PGI$_2$ sodium salt as defined in claim 1.

15. 2,3,4-Trinor-1,5-inter-m-phenylene-16-tosylamino-PGI$_2$ sodium salt as defined in claim 1.

16. 2,3,4,17,18,19,20-Heptanor-1,5-inter-m-phenylene-16-amino-16-phenyl PGI$_2$ sodium salt as defined in claim 1.

17. 2,3,4,18,19,20-Hexanor-1,5-inter-m-phenylene-16-amino-17-phenyl-PGI$_2$ sodium salt as defined in claim 1.

18. 5(Z)-2,3,4,17,18,19,20-Heptanor-1,5-inter-m-phenylene-16-phenoxy-PGI$_2$ dicyclohexylamine salt as defined in claim 1.

19. 5(Z)-2,3,4,17,18,19,20-Heptanor-1,5-inter-m-phenylene-16-phenoxy-PGI$_2$ ammonium salt as defined in claim 1.

20. 5(Z)-2,3,4,17,18,19,20-Heptanor-1,5inter-m-phenylene-16-phenoxy-PGI$_2$ dimethylamine salt as defined in claim 1.

21. 5(Z)-2,3,4,17,18,19,20-Heptanor-1,5-inter-m-phenylene-16-phenoxy-PGI$_2$ tetrabutylammonium salt as defined in claim 1.

22. 5(Z)-2,3,4,17,18,19,20-Heptanor-1,5-inter-m-phenylene-16-phenoxy-PGI$_2$ tris(hydroxymethyl)-methylammonium salt as defined in claim 1.

23. A pharmaceutical composition with blood platelet aggregation inhibiting effect, characterized by containing as active agent a blood platelet aggregation inhibiting amount of the compound of the formula (I), wherein R$^1$, R$_2$, R$_3$, R$_4$ and R$^5$ are as defined in claim 1, together with a conventional pharmaceutical carrier, diluent, formulation and and/or other additive.

24. A method of inhibiting blood platelet aggregation in a susceptible subject which comprises administering to said subject an effective amount of a compound as defined in claim 1.

* * * * *